United States Patent [19]

Markussen

[11] Patent Number: 4,946,828

[45] Date of Patent: Aug. 7, 1990

[54] NOVEL INSULIN PEPTIDES

[75] Inventor: Jan Markussen, Herlev, Denmark

[73] Assignee: Novo Nordisk A/S, Bagsvaerd, Denmark

[21] Appl. No.: 75,387

[22] Filed: Jul. 20, 1987

Related U.S. Application Data

[63] Continuation-in-part of Ser. No. 838,472, Mar. 11, 1986, abandoned.

[30] Foreign Application Priority Data

| Mar. 12, 1985 | [DK] | Denmark | 01135/85 |
| Mar. 11, 1986 | [DK] | Denmark | 01070/86 |
| Jul. 21, 1986 | [DK] | Denmark | 03470/86 |

[51] Int. Cl.$^5$ .................. A61K 37/26; C07K 7/40
[52] U.S. Cl. ........................... 514/3; 530/303
[58] Field of Search ..................... 530/303; 514/3

[56] References Cited

U.S. PATENT DOCUMENTS

| 3,528,960 | 9/1970 | Haas | 530/303 |
| 3,884,897 | 5/1975 | Geiger et al. | 530/303 |
| 4,608,364 | 8/1986 | Gran | 514/4 |

FOREIGN PATENT DOCUMENTS

| 84108442.9 | 2/1985 | European Pat. Off. |
| 0163529 | 12/1985 | European Pat. Off. |
| 2042299 | 3/1972 | Fed. Rep. of Germany |
| 3326473 | 1/1985 | Fed. Rep. of Germany |
| 3327709 | 2/1985 | Fed. Rep. of Germany |
| 55-144032 | 4/1982 | Japan |

OTHER PUBLICATIONS

Markussen et al., Protein Engineering, vol. 1, No. 3, pp. 205–213; 215–233 (1987).
Glimeher et al., The Journal of Immunology, vol. 131, No. 6, pp. 2868–2874 (1983).
Knud Hallas-Møller: Chemical and Biological Insulin Studies, Copenhagen, 1945, vol. 1, pp. 180–184.
Geiger & Enzmann: Clinical Application of Insulin Derivatives, Amsterdam-Oxford, 1979, pp. 306–310.
D. A. Scott and A. M. Fisher: The Effect of Zinc Salts on Action of Insulin, J. Pharmacol., 55 (1935), pp. 206–221.

Primary Examiner—Lester L. Lee
Assistant Examiner—Christina Chan
Attorney, Agent, or Firm—Morris Fidelman; Franklin D. Wolffe

[57] ABSTRACT

Insulin derivatives having a charge which is positive compared with the charge of human insulin at neutral pH, can be used to prepare solutions having prolonged insulin action. In the novel insulin derivatives, a basic amino acid has been substituted in the B27-position and/or a neutral amino acid has been inserted in the A4-, A17-, B13- and/or B21-position. Furthermore, the C-terminal carboxyl group of the B-chain may be blocked with an amido or ester residue.

7 Claims, No Drawings

NOVEL INSULIN PEPTIDES

This application is a continuation in part of Ser. No. 838,472, filed Mar. 11, 1986 and now abandoned.

BACKGROUND OF THIS INVENTION

The present invention relates to novel insulin compounds and to novel injectable solutions having prolonged insulin action.

In the treatment of diabetes mellitus, many varieties of insulin preparations have been suggested and used. Some of the preparations are fast acting and other preparations have more or less prolonged actions. Usually, pharmaceutical insulin preparations with more or less prolonged action are desirable. Such a prolonged action may be obtained by administering the insulin as a suspension of insulin crystals. The crystalline preparations can be obtained by crystallization of insulin in the presence of zinc (such as LENTE TM, see Schlichtkrull: Insulin Crystals, Chemical and Biological Studies on Insulin Crystals and Insulin Zinc Suspensions, Munksgaard, 1958) or by crystallization of insulin in the presence of zinc and protamine (such as NPH-insulin, see Rep.Steno Mem.Hosp. 1 (1946), 60).

One disadvantage in the use of the known suspensions of zinc insulin crystals or of zinc protamine insulin is the necessity of shaking the vial in order to ensure that the correct amount of insulin is being injected and to ensure that the concentration of insulin in the vial remains constant throughout its use. In PENFILL TM cartridges where air must be absent, prolonged acting insulin suspensions require the incorporation of a solid body in the cartridge to enable agitation. The shaking of insulin suspensions and insulin solutions with air is in itself an undesirable process, as insulin has a tendency to denature under formation of fibrils at water-air interfaces. Consequently, solutions of insulins with prolonged action are desirable.

Solutions of insulin derivatives having a prolonged action was obtained from insulin that had been modified in its amino groups by reaction with phenylisocyanate (so-called Isoinsulin, see Hallas-Moeller: Chemical and Biological Insulin Studies based upon the Reaction between Insulin and Phenylisocyanate, Copenhagen 1945). Similarly, A1,B29-di-Boc substituted insulin (Boc designates tertiary butyloxycarbonyl) was reported to show a prolonged insulin action after subcutaneous administration (see Geiger & Enzmann in: Proinsulin, Insulin, C-peptide; Proceedings of the Symposium on Proinsulin, Insulin and C-Peptide, Tokushima 1978; Amsterdam-Oxford 1979, 306–310). The A1,B29-di-Boc substituted insulin was found to exhibit a too slightly prolonged action to be clinically useful.

Solutions of unmodified insulins require large amounts of zinc ions (for example, 0.4–1 mg/U insulin) in order to exhibit a prolonged action (see J.Pharmacol. 55 (1935), 206). Injection of such large doses of zinc ions will probably cause pain and such solutions have, therefore, never been used in therapy.

The isoelectric point of insulin is about 5.5 and attempts have been made to decrease the solubility of insulin derivatives at neutral pH by shifting the isoelectric point upwards, for example, through additions, in the N-terminus of the B-chain, of basic amino acids like lysine or arginine (see, for example, German Offenlegungsschrift No. 2,042,299) or with the basic dipeptide arginyl-arginine (see Geiger & Enzmann cited above). The solubility of the latter compound, $Arg^{B(-1)}$-$Arg^{B0}$ insulin, near its isoelectric point was, however, much higher than that of the parent insulin.

Japanese patent application No. 55-144032 relates to analogues to human insulin wherein the B30-amino acid has been replaced by an amino acid having at least five carbon atoms, and amides and esters thereof These insulin analogues were to be used in patients who had developed antibodies against mammalian insulins. In the Japanese patent application, six specific compounds are described, none of which were stated to have prolonged action. No specific injectable preparations are described in the Japanese patent application.

European patent application No. 84108442.9 relates to insulin analogues wherein a basic, organic group is attached to the B30-amino acid thereby introducing a positive charge at neutral pH. In these analogues, the B30-amino acid is neutral and, preferably, threonine as in human insulin. German patent application No. 3,327,709.5 relates to a suspension of crystals of the derivatives described in the above-noted European patent application as well as an aromatic hydroxy compound German patent application No. 3,326,473.2 relates to a medicament containing a mixture of insulin compounds, of which at least one is described in the above-noted European patent application.

BRIEF STATEMENT OF THE INVENTION

The present invention comprises novel analogs of human insulin that differ from human insulin by:

(a) having at least one charge more than human insulin at pH 7, preferably not more than 4 charges more than human insulin at pH 7 and, (b) optional presence of an amide or ester residue on the C-terminal carboxyl group of the B-chain.

The change in charge is achieved by substituting one or more of the amino acids compared with human insulin, and if desired by blocking of the carboxylic group in the B30 amino acid.

In specific, the compounds of interest to practice of this invention are characterizable as follows: One or more of the four glutamic acid residues at A4, A17, B13, B21 is instead another naturally occurring neutral amino acid, preferably glutamine; and/or the threonine residue at B27 is instead a naturally occurring basic amino acid residue, preferably L-arginine or L-lysine. Optionally, the threonine residue at B30 is instead one or two basic amino acid residues, one being preferred. The C terminal carboxylic group in the B chain may be protected.

The invention also comprises solutions of the above categorized insulin analogs with a controlled concentration of zinc ions therein. The degree of prolongation of insulin action is enhanced as the zinc concentration is increased.

DETAILED PRACTICE OF THIS INVENTION

It has surprisingly been found that injectable solutions with a combined short and prolonged insulin action can be made using, as the active ingredient, a single insulin derivative having the general formula I

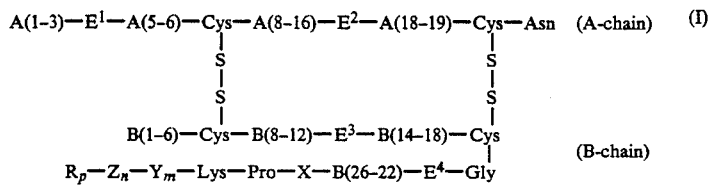

wherein the letters A and B followed by figures in parentheses designate the peptide fragments of the A- and B-chains, respectively, indicated by the figures in parentheses, $E^1$, $E^2$, $E^3$ and $E^4$ are the same or different each representing glutamic acid or a neutral amino acid residue which can be coded for by nucleotide sequences, X represents an L-threonine, L-arginine or L-lysine residue, Y and Z are the same or different and each represent an amino acid residue wherein any side chain amino group may be acylated and wherein any side chain hydroxy group may be alkylated, m, n and p are the same or different and each represent zero or one, and R represents an amid-o or ester residue which blocks the C-terminal carboxyl group of the B-chain, with the proviso that the amino acids $E^1$, $E^2$, $E^3$, $E^4$, X, Y and Z and the group R are selected so that, compared with human insulin, the compound of formula I has at least one charge more at a pH value of 7, and with the further proviso that if $E^1$, $E^2$ and $E^4$ each is Glu, and X and $-Y_m-Z_n-R_p$ each is Thr, then $E^3$ is different from Glu, and with the still further proviso that X is arginine or lysine, if each of the four amino acid residues $E^1$, $E^2$, $E^3$ and $E^4$ are glutamic acid residues.

Specific examples of the group of formula $-Y_m-Z_n-R_p$ are $-NH_2$, $-Arg-NH_2$, $-Arg-Arg-NH_2$, $-Arg-Lys-NH_2$, $-Dab-Dab-NH_2$, $-Dap-Dap-NH_2$, $-Lys-NH_2$, $-Lys(Lau)-NH_2$, $-Lys-Arg-NH_2$, $-Lys-Lys-NH$ , $-Orn-NH_2$, $-Orn-Orn-NH_2$, $-Thr-NH_2$, $-Thr-OBu^t$ or $-Thr(Bu^t)-OBu^t$. Lau designates lauroyl, and Dab and Dap represents $\alpha,\gamma$-diaminobutyric acid and $\alpha,\beta$-diaminopropioic acid, respectively.

A subgroup of compounds of formula I is compounds of the general formula I, wherein p is one.

Compared with insulin, the change in charge is obtained by substituting the threonine residue in the B27-position with arginine or lysine and/or by substituting any of the four glutamic acid residues in the A4-, A17-, B13-, and B21-position with a neutral amino acid, preferably with a glutamine residue. In addition, the C-terminal carboxyl group of the B-chain may be blocked by an ester group or amide group thereby eliminating the negative charge of the carboxyl group. Furthermore, a positive charge may be introduced by inserting a basic amino acid in the B30- and/or B31-position. Since compounds of formula I can be applied in the clinic as solutions having a prolonged action, a decline in immunogenicity as compared to the commonly used suspensions of porcine or human insulins may occur.

The degree of prolongation can be enhanced and controlled by the addition of zinc ions.

Major parameters that control the degree of prolongation of the insulin effect are the concentration of zinc and the choice of the compound of formula I. With some analogs, e.g. $Arg^{B27}, Thr^{B30}-NH_2$ human insulin, very prolonged action is obtained with only 3 zinc atoms per hexamer unit of insulin analog corresponding to 8 µg zinc/ml in a preparation containing about 240 nmole/ml. With other analogs, e.g. $Lys^{B30}-NH$ human insulin, moderate prolongation of action is obtained with 30 zinc per hexamer of insulin analog corresponding to 80 µg zinc/ml in a preparation containing about 240 nmole/ml. The range for preferred zinc contractions extends from 0 to 2 mg/ml, preferably from 0 to 200 µg/ml zinc with substitution in the B13 and/or B27 position, more preferably from 20 to 200 µg/ml with other analogs, in a preparation containing 240 µmole of a compound of formula I per ml.

The prolonged action of solutions of compounds of formula I in the presence of zinc ions may be ascribed to the low solubility of such compounds at neutral pH. Solutions of insulin derivatives in which the C-terminal of the B-chain was blocked, showed a special preferred prolonged action.

The pH of the injectable solution of this invention should preferably be below the physiological pH value, the upper limit being the pH value where precipitation occurs. Stable solutions containing about 240 nmole/ml of compounds of formula I have been obtained at pH 5.5. The upper limit depends upon the constituents of the solution, i.e., isotonic agent, preservative and zinc concentration, and upon the choice of compound of formula I. There is no lower pH limit of the solutions, but since the chemical stability of insulins is poor in acid solutions due to deamidation reactions and formation of dimers, as high a pH as possible with respect to the physical stability of the solution is preferred. The preferred pH range for the injectable solutions of this invention is from 2.5 to 8.5, more preferred from 4.5 to 8.

A further aspect of this invention is that it provides improved flexibility for the patients With two aqueous solutions, one containing a compound of formula I and the other containing a zinc salt, the patient can obtain a desired degree of prolonged action and a desired profile by mixing the two solutions appropriately. Thus, the patient has, using two stock solutions, the possibility of choosing one action and profile for the morning injection and another action and profile for the evening injection. Preferably, the zinc solution contains between about 10 µg and 20 mg zinc per ml. Alternatively, both of the stock solutions may contain zinc, either in the same or different concentrations, and/or both the stock solutions may contain a compound of formula I, either the same or different compounds.

Preferably, the injectable solutions of this invention have a strength of between about 60 and 6000 nmole/ml of the compound of formula I.

The neutral amino acid ($E^1$ through $E^4$) is, for example, glycine, valine, isoleucine, leucine, phenylalanine, tyrosine, methionine or preferably asparagine, glutamine, alanine, serine or threonine.

Examples of R are ester moieties, for example, lower alkoxy, preferably methoxy, ethoxy and most preferred tertiary butoxy, and such groups are present in compounds which are useful in the synthesis of human insulin, see, for example, U.S. Pat. No. 4,343,898. Such esters are Thr$^{B30}$—OBu$^t$ human insulin and Thr$^{B30}$(Bu$^t$)—OBu$^t$ human insulin (Bu$^t$ designates tertiary butyl).

Furthermore, R can be a group of the general formula —NR$^1$R$^2$ wherein R$^1$ and R$^2$ are the same or different and each represents hydrogen or lower alkyl. Hereinafter the term "lower" designates that the group in question contains less than 7 carbon atoms, preferably less than 5 carbon atoms. An example of such a group is found in Thr$^{B30}$—NH$_2$ human insulin which is known as an intermediate in a synthesis of human insulin (see Carlsberg Res.Commun. 49 (1984), 463). In a preferred embodiment of this invention, R is —NH$_2$. Furthermore, R may be a lactam residue which preferably contains less than 8 atoms in the lactam ring, for example a lactam of a diaminocarboxylic acid.

In a preferred embodiment of this invention, R is uncharged.

At neutral pH, the charge of —X$^{27}$—Pro$^{28}$—Lys$^{2-}$9—Y$_m$—Z$_n$—R$_p$ is +1 in Lys$^{B29}$—NH, des-(B30) human insulin, +2 in Lys$^{B27}$,Thr$^{B30}$—NH human insulin and Arg$^{B27}$,Thr$^{B30}$—NH$_2$ human insulin, and +3 in Lys$^{B27}$,Lys$^{B30}$—NH$_2$ human insulin, Lys$^{B27}$,Arg$^{B30}$—NH$_2$ human insulin, Arg$^{B27}$,Lys$^{B30}$—NH$_2$ human insulin and Arg$^{B27}$,Arg$^{B30}$—NH$_2$ human insulin.

According to one preferred embodiment of this invention, the amino acid residues designated Y and Z are residues from L-amino acids which are coded for by nucleotide sequences.

Any side chain amino group in the amino acid residues designated Y and Z may be acylated by an acid containing from 2 to 18 carbon atoms, preferably a fatty acid containing from 6 to 18 carbon atoms, for example, lauric acid. Thus, —Y$_m$—Z$_n$—R$_p$ may be —Lys(Lau)—NH$_2$.

Examples of preferred alkylated hydroxy groups are methoxy, ethoxy and tertiary butoxy.

In one group of preferred compounds of formula I, Y and/or Z is a basic amino acid residue wherein the side chain amino group optionally is acylated (m=1).

In another group of preferred compounds of formula I, n is zero and Y is a basic amino acid residue (m=1).

In a further group of preferred compounds of formula I, Y and Z are both basic amino acid residues (m=1, n=1).

Preferred compounds of formula I are each of the following: Gln$^{A17}$,Arg$^{B27}$,Thr$^{B30}$—NH$_2$ human insulin, Gln$^{A17}$, Gln$^{B13}$,Thr$^{B30}$—NH$_2$ human insulin, Gln$^{A17}$,Lys$^{B27}$,Thr$^{B30}$—NH insulin, Gln$^{A17}$,Lys$^{B30}$—NH$_2$ human insulin, Gln$^{A17}$,Thr$^{B30}$—NH$_2$ human insulin, Gln$^{B13}$,Arg$^{B27}$,Thr$^{B30}$—NH$_2$ human insulin, Gln$^{B13}$,Lys$^{B27}$,Thr$^{B30}$—NH$_2$ human insulin, Gln$^{B13}$,Lys$^{B30}$—NH$_2$ human insulin, Gln$^{B13}$,Thr$^{B30}$—NH$_2$ human insulin, Arg$^{B27}$,Arg$^{B30}$—NH$_2$ human insulin, Arg$^{B27}$Lys$^{B30}$—NH$_2$ human insulin, Arg$^{B27}$,Thr$^{B30}$—NH$_2$ human insulin, Lys$^{B2-7}$,Arg$^{B30}$—NH$_2$ human insulin, Lys$^{B27}$,Lys$^{B30}$—NH$_2$ human insulin and Lys$^{B27}$,Thr$^{B30}$—NH$_2$ human insulin.

Another preferred embodiment of this invention is preparations containing a compound of formula I wherein E$^1$, E$^2$, E$^3$ and/or E$^4$ is a glutamine residue, and/or X is Lys or Arg, and within this subclass of compounds of formula I, a further preferred embodiment is preparations containing a compound of formula I wherein the group —Y$_m$—Z$_n$—R$_p$ is —Thr—NH$_2$ or —Lys—NH$_2$. Especially, preferred compounds are Thr$^{B30}$—NH$_2$ human insulin, Gln$^{A17}$,Thr$^{B30}$—NH$_2$ human insulin, Lys$^{B27}$,Th$^{B30}$—NH$_2$ human insulin and Arg$^{B27}$,Thr$^{B30}$—NH$_2$ human insulin.

Further preferred embodiment of this invention is compounds containing a compound of formula I, in which m is one, n is zero, and Y is threonine. One subgroup of compounds within the last-mentioned, preferred compounds is compounds wherein p is zero, and specific examples of such compounds are Lys$^{B27}$ human insulin, Arg$^{B27}$ human insulin, Gln$^{A17}$,Arg$^{B27}$ human insulin, Gln$^{A17}$,Gln$^{B13}$ human insulin, Arg$^{B27}$,Gln$^{B13}$ human insulin, Gln$^{A17}$,Lys$^{B27}$ human insulin and Gln$^{B13}$,Lys$^{B27}$ human insulin.

In one group of preferred compounds of formula I, E$^1$, E$^3$ and E$^4$ is each a glutamic acid residue.

In another group of preferred compounds of formula I, E$^2$ is a glutamine residue.

In a still further group of preferred compounds of formula I, X is an arginine or lysine residue.

As is well known in the art, not all of the amino acid residues in human insulin are essential for the insulin action. Indeed, porcine insulin and bovine insulin which differs from human insulin in amino acid residues have been employed to treat diabetics. Considerable species to species variations in the insulin molecule exist. Thus, many amino acid residues in the insulin molecule may be changed without undue diminution in insulin activity, including some amino acid residues that influence the isoelectric point of the molecule.

It is obvious that the groups designated E$^1$, E$^2$, E$^3$, E$^4$, X, Y, Z and R are to be selected so that the resulting compound of formula I is pharmaceutically acceptable.

In the known biphasic insulin preparations, it is common to combine fast acting, soluble insulin with prolonged acting, crystalline insulin in the same injection. Using compounds of formula I of this invention, a similar combined short and prolonged action can be obtained with a solution of a single compound of formula I. The ratio between fast and long effect decreases as the concentration of zinc ions in the solution is increased.

Compounds of formula I may be prepared by a transpeptidation reaction in which a biosynthetic precursor compound having the correct insulin disulphide bridges and having the general formula II:

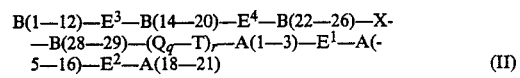

$$B(1-12)-E^3-B(14-20)-E^4-B(22-26)-X-\\-B(28-29)-(Q_q-T)_r-A(1-3)-E^1-A(-\\5-16)-E^2-A(18-21) \quad (II)$$

wherein Q is a peptide chain with q amino acids, q is an integer from 0 to 33, T is Lys or Arg, r is zero or one, and A, B, E$^1$, E$^2$, E$^3$, E$^4$ and X each are as defined above, is reacted with an amino compound of the general formula III:

$$H-Y_m-Z_n-R_p \quad (III)$$

wherein Y, Z, R, m, n and p each are as defined above, and wherein side chain amino groups and hydroxy groups in Y and Z optionally are blocked with amino and hydroxy protecting groups, using trypsin or a trypsin like enzyme as a catalyst in a mixture of water and organic solvents as has been described in U.S. Pat. No. 4,343,898. Preferred compounds of formula III for use in this process are Thr—NH$_2$, Lys(Boc)—NH$_2$, Thr(Bu$^t$)—OBu$^t$, Thr—OBu$^t$, Ala—NH$_2$ and Arg(Boc)—NH$_2$. Amino groups may be derivatized by acylation with a fatty acid. Hydroxy groups may be protected by alkylation. If Y and Z contain groups which are reversibly blocked by amino protecting groups, these groups may be removed at a later stage, if such is desired, after the amino protected intermediate has been separated from the trypsin or trypsin like enzyme. Of the trypsin like enzymes, lysyl endopeptidase from *Achromobacter .lyticus* is useful.

The compound of formula II may be expressed in a host organism such as yeast similar to the description in European patent application publication No. 163,529 of which the U.S. counterpart is Ser. No. 739,123, filed May 29, 1985 using a gene having the correct codons for the amino acids in question. The gene encoding the novel insulin derivative is then inserted into a suitable expression vector which when transferred to yeast is capable of expressing the desired compound. The product expressed is then isolated from the cells or the culture broth depending on whether it is secreted from the cells or not.

An example of a reversible amino protecting group is tertiary butoxycarbonyl and a reversible hydroxy protecting group is tertiary butyl. Such groups are removed under conditions which do not cause undesired alteration in the compound of formula I, for example, by trifluoroacetic acid.

Insulin compounds of formula I may also be prepared by a coupling reaction in which a compound of the general formula IV medium is made isotonic, for example, with sodium chloride or glycerol Furthermore, the aqueous medium may contain zinc ions in a concentrations of up to about 20 μg of $Zn^{++}$ per unit of insulin activity, buffers such as acetate and citrate and preservatives such as m-cresol or phenol. The pH value of the solution is adjusted towards neutrality without getting too close to the isoelectric point of the compound of formula I in order to avoid precipitation. The pH value of the final insulin preparation depends upon the number of charges that have been changed in the compound of formula I, the concentration of zinc ions, the concentration of the compound of formula I and the compound of formula I selected. The insulin preparation is made sterile by sterile filtration.

The insulin preparations of this invention are used similarly to the use of the known insulin preparations.

Any novel feature or combination of features described herein is considered essential to this invention.

Herein the abbreviations used for the amino acids are those stated in J.Biol.Chem. 243 (1968), 3558. The amino acids stated herein are in L configuration. In formula I and elsewhere herein A(1—3) is Gly—Ile—Val, A(5—6) is Gln—Cys etc , cf. the amino acid sequence of human insulin Unless otherwise indicated, the species of insulins stated herein is human.

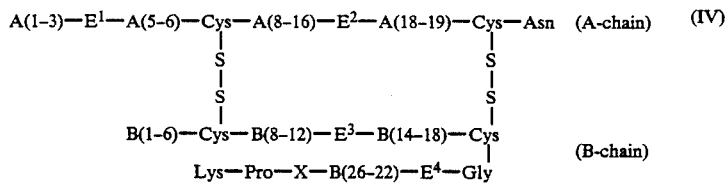

(IV)

wherein $E^1$, $E^2$, $E^3$, $E^4$ and X each are as defined above, is coupled to an amino compound of the above formula III by trypsin or a trypsin like enzyme under conditions similar to those described in European patent specification publication No. 17,938.

When insulin is manufactured by genetic engineering the additional one or two positive charges may appropriately be introduced internally in the insulin molecule, i.e., in the A4—, A17—, B13—, B21— or B27—position, leaving for trypsin catalyzed semisynthesis blocking of the C-terminal carboxyl group of the B-chain with an amino acid amide or an amino acid ester.

The advantage in introducing the additional positive charges within the frame of the 51 amino acids of the insulin molecule to form the novel compounds of formula I rather than by prolongation of the B-chain beyond the 30 residues of the mammalian insulins relates to ease in preparation. In the semisynthetic transpeptidation a large molar excess of the amino acid amide or amino acid ester is employed. If a dipeptide amide or ester were to be used in the transpeptidation reaction, either price or solubility or both are prohibitive for use in large excess, and consequently the yield of the product becomes lower. Even when the same equimolar excess of, for example, Lys(Boc)—$NH_2$ and Lys(Boc)—Lys(Boc)—$NH_2$ is used in the transpeptidation reaction under similar conditions, the yield with the amino acid amide becomes substantially higher than with the dipeptide amide.

Insulin preparations of this invention are prepared by dissolving a compound of formula I in an aqueous medium at slightly acidic conditions, for example, in a concentration of 240 or 600 nmole/ml. The aqueous Synthesis of the insulin compounds The source of insulin was an insulin precursor expressed in yeast as described in the last-mentioned Danish patent application (see also European Patent Application Publication No. 163.52*).

The insulin precursors were recovered from the fermentation broths by adsorption LICHROPREP TM RP-18 as described in Example 7 of the same Danish patent application. The precursors were eluted from the column with 0.2M KCl, 0.001M HCl in 33% (v/v) ethanol. The insulin precursors were crystallized from the pool by successive additions of water (1 volume per volume of pool), solid trisodium citrate to make 0.05M and finally zinc acetate to make 0.006M. The pH was adjusted to 6.8 and the mixture was left overnight at 4° C. The crystals were isolated by centrifugation, washed with water and dried in vacuo.

Protected amino acids and protected peptides for enzymatic semisynthesis were either prepared by standard methods or purchased (custom synthesis) from either Nova Biochem or Bachem, both Switzerland.

The letters TM after a name indicates that it is a trade mark.

In the starting material in Examples 1 through 13 $(Q_q—T)_r$ of formula II was chosen to Ala—Ala—Lys and constructed as described for yeast plasmid pMT610 in Example 10 in Danish patent application No. 582/85. Nucleotides coding for $Gln^{B13}$, $Gln^{A17}$, $Arg^{B27}$ and $Lys^{B27}$ were substituted in pMT610 by site specific mutagenesis using the procedure in Nucl.Acids.Res. 11 (1983), 5103–5112.

EXAMPLE 1

Synthesis of Gln$^{B13}$,Arg$^{B27}$ human insulin

To a suspension of 5 g of Gln$^{B13}$,Arg$^{B27}$,B(1—29-)—Ala—Ala—Lys—A(1—21) insulin precursor in 50 ml of 2M Thr—OBu$^t$,CH$_3$COOH (L—threonine tert-.butyl ester, hydroacetate salt) in DMF, 25 ml of 25.5% (v/v) water in DMF (25.5 ml water, DMF to make 100 ml) was added. The suspension was cooled to 12° C. under stirring. A solution of 0.5 g of porcine trypsin in 12.5 ml of a 0.05M aqueous solution of calcium acetate was added. Stirring was continued until dissolution. After 48 hours at 12° C., the proteins were precipitated by pouring the mixture into 600 ml of acetone. The precipitate was isolated by centrifugaton, washed once with 200 ml of acetone, isolated by centrifugation and dried in a stream of nitrogen. The precipitate was dissolved in 100 ml of 0.04N hydrochloric acid, the pH value was adjusted to 2.5 and the solution was applied to a 5×30 cm preparative high pressure liquid chromatography (hereinafter designated HPLC) column packed with silica particles substituted with octadecyl-dimethylsilyl (mean particle size 15 micron, pore size 100 Ångstrom). The column was equilibrated with ethanol/0.3M aqueous solution of potassium chloride, 0.001N hydrochloric acid, in a ratio of 35.5/64.5 (parts per volume). The proteins were eluted from the column with the same buffer at a rate of 2 liter/h. Gln$^{B13}$,Arg$^{B27}$,Thr$^{B30}$—OBu$^t$ human insulin was found in a peak emerging from the column between 55 and 100 min. The Gln$^{B13}$,Arg$^{B27}$,Thr$^{B30}$—OBu$^t$ human insulin was isolated from the pool by successive additions of water to make ethanol concentration 15% (v/v), solid trisodium citrate to obtain a molarity of 0.05M with respect to citrate and solid zinc chloride to obtain a molarity of 0.006M with respect to zinc. The pH value was adjusted to 6.8 and after 1 hour at room temperature, the crystallisation was continued at 4° C. for 24 hours with stirring. The crystals were spun down, washed twice with 20 ml of ice-cold water, spun down and dried in vacuo.

Yield: 2.51 g of Gln$^{B13}$,Arg$^{B27}$,Thr$^{B30}$—OBut human insulin.

Gln$^{B13}$,Arg$^{B27}$,Thr$^{B30}$—OBu$^t$ human insulin was dissolved in 100 ml of trifluoroacetic acid and left for 2 hours at room temperature. The trifluoroacetic acid was removed by lyophilization. The lyophilisate was dissolved in 100 ml of water, the pH value adjusted to 2.5 and 20 g of sodium chloride was added. The salt cake consisting of Gln$^{B13}$,Arg$^{B27}$ human insulin was isolated by centrifugation. The salt cake was dissolved in 850 ml of water and Gln$^{B13}$,Arg$^{B27}$ human insulin was crystallized by successive additions of 150 ml of ethanol, 14.7 g of trisodium citrate,dihydrate and 0.82 g of zinc chloride followed by adjustment of the pH value to 6.8. After 1 hour at room temperature, the crystallisation was continued at 4° C. for 24 hours with gentle stirring. The crystals were spun down, washed twice with 20 ml of ice-cold water, spun down and dried in vacuo. Yield: 1.71 g of Gln$^{B13}$,Arg$^{B27}$ human insulin, corresponding to 36%.

The amino acid composition was in agreement with the theory, arginine being 2 residues/molecule. The product was pure in DISC PAGE electrophoresis, the rate of migration being 55% of that of human insulin corresponding to a difference in charges of about 2. For details of the DISC PAGE electrophoresis see Horm.Metab.Res. Supplement Series No. 5 (1974), 134. The content of zinc in the crystals was 0.42% (weight/weight).

EXAMPLES 2-5

Synthesis of Gln$^{B13}$,Gln$^{A17}$ human insulin, Gln$^{A17}$,Arg$^{B27}$ human insulin, Arg$^{B27}$ human insulin and Lys$^{B27}$ human insulin The 4 title compounds were synthesized from the corresponding single chain insulin precursors, viz.

Gln$^{B13}$,Gln$^{A17}$,B(1—29)—Ala—Ala—Lys—A(1—21),

Gln$^{A17}$,Arg$^{B27}$,B(1—29)—Ala—Ala—Lys—A(1—21),

Arg$^{B27}$,B(1—29)—Ala—Ala—Lys—A(1—21) and

Lys$^{B27}$,B(1—29)—Ala—Ala—Lys—A(1—21), using the methods described in Example 1. Yields, charges relative to human insulin, rates of migration relative to insulin in DISC PAGE electrophoresis at pH 8.9 and deviations in amino acid compositions from human insulin appear from Table I, below.

TABLE I

| Substitution in human insulin | Yield % | Charge relative to human insulin at pH 7 | Rate of migration at pH 8.9, % relative to human insulin | Deviations in amino acid compositions from human insulin after acid hydrolysis, residues/molecule |
|---|---|---|---|---|
| Gln$^{B13}$,Gln$^{A17}$ | 46 | +2 | 55 | none |
| Gln$^{A17}$,Arg$^{B27}$ | 32 | +2 | 55 | +1 Arg, −1 Thr |
| Arg$^{B27}$ | 35 | +1 | 75 | +1 Arg, −1 Thr |
| Lys$^{B27}$ | 39 | +1 | 75 | +1 Lys, −1 Thr |

EXAMPLE 6

Synthesis of Gln$^{A17}$,Thr$^{B30}$—NH$_2$ human insulin

To a suspension of 3.12 g of Gln$^{A17}$,B(1—29-)—Ala—Ala—Lys—A(1—21) insulin precursor in 15 ml of acetic acid/DMF/water (11.4 ml acetic acid, 65.1 ml DMF, water to make 100 ml) 30 ml of 1M Thr-NH$_2$ in DMF was added. The mixture was cooled to 12° C. and 0.3 g of porcine trypsin dissolved in 7.5 ml of 0.05M calcium acetate was added. Stirring was continued until the insulin precursor had dissolved. After 48 hours at 12° C. the proteins were precipitated by addition of 400 ml of acetone. The proteins were isolated by centrifugation, washed once with 100 ml of acetone and dried in vacuo.

The precipitate was dissolved in 70 ml of 0.04N HCl, the pH adjusted to 2.5 and the derivative was purified by HPLC by an eluent composed of 35 parts of ethanol and 65 parts of 0.3M KCl, 0.001N HCl. The derivative emerged from the column after about 3 column volumes, and it was isolated by successive additions of 1 volume of water, solid trisodium citrate to make 0.05M and solid zinc acetate to make 0.006M. After adjustment of pH to 6.5 and stirring overnight at 4° C., crystals were harvested by centrifugation, washed with water and dried. Yield 1.64 g=53%. Further purifications by anion exchange chromatography as described for human insulin esters (see Markussen, ibid, 410). Final yield: 1.15 g=37%. The product was near homogeneous in DISC PAGE electrophoresis at pH 8.9, the rate of migration being 55% of that of insulin. In analytical reverse-phase HPLC (see Markussen ibid, 410) the product elutes at about the same rate as porcine insulin.

EXAMPLE 7

Synthesis of $Gln^{A17}, Lys^{B30}-NH_2$ human insulin

To a suspension of 3.15 g of $Gln^{A17}, B(1-29)$-Ala—Ala—Lys—A(—21) insulin precursor in 15 ml of acetic acid/DMF/water (4.57 ml acetic acid, 71.9 ml of DMF, water to make 100 ml) 30 ml of 0.4M Lys(-Boc)—$NH_2$ in DMF was added. The mixture was cooled to 12° C. and 0.3 g of trypsin dissolved in 7.5 ml of 0.05M calcium acetate was added. Stirring was continued until the insulin precursor had dissolved. After 48 hours at 12° C. the proteins were isolated as described in Example 6.

The precipitate was dissolved in 70 ml of 0.04N HCl, the pH adjusted to 2.5 and $Gln^{A17}, Lys(Boc)^{B30}-NH_2$ human insulin was purified by HPLC as described in Example 1, except that elution was performed first with 2.3 1 of an eluent composed of 37 parts ethanol and 63 parts of 0.3M KCl, 0.001N HCl, followed by an eluent composed of 39 parts of ethanol and 61 parts of aqueous 0.3M KCl, 0.001N HCl. The derivate emerged 25 minutes after the change of eluent, and it was isolated as described for $Gln^{A17}, Thr^{B30}-NH_2$ human insulin in Example 4. Yield of $Gln^{A17}, Lys(Boc)^{B30}-NH_2$ human insulin 906 mg=29%.

$Gln^{A17}, Lys(Boc)^{B30}-NH_2$ human insulin (1.55 g) was dissolved in 30 ml of trifluoroacetic acid (TFA) and left at room temperature for 2 hours. The TFA was removed by lyophilization. The residue was dissolved in 15 ml of water, the pH adjusted to 3 with 1N NaOH and 22 ml of ethanol was added. The solution was applied to a 2.5×20 cm column of SP-SEPHADEX ™ C-25 equilibrated with an ethanol/water 3/2 (v/v) buffer comprising 0.01M citric acid, 0.03M NaCl, pH adjusted to 4.5 with NaOH. The column was eluted with the same buffer, using a linear gradient in NaCl from 0.03M to 0.4M in a total of 1.6 1 of eluent. The derivative eluted in 440 ml when the gradient reached 0.2M NaCl. It was crystallized by addition of 1100 ml of water, solid trisodium citrate to make 0.05M and solid zinc acetate to make 0.006M. Eventually the pH was adjusted to 6.8. After stirring overnight at 4° C. the crystals were isolated by centrifugation, washed once with water and dried in vacuo. Yield: 1.00 g corresponding to 65% over last step and 19% from the $Gln^{A17}, B(1-29)$—Ala—Ala—Lys—A(1—21) insulin precursor. The product was near homogeneous in DISC PAGE electrophoresis at pH 8.9, the rate of migration being 35% of that of insulin. In analytical HPLC the product emerges before porcine insulin, the purity being about 97%. Amino acid composition analysis showed 2 lysine and 2 threonine residues per molecule, and otherwise identity to human insulin.

EXAMPLE 8

Synthesis of $Arg^{B27}, Thr^{B30}-NH_2$ human insulin

To a suspension of 3.8 g of $Arg^{B27}, B(1-29)$-Ala—Ala—Lys—A(1—21) insulin precursor in 18 ml of acetic acid/water/DMF (11.4 ml acetic acid, 35 ml water, DMF to make 100 ml) 36 ml of 1M Thr—$NH_2$ in DMF was added. The mixture was cooled to 12° C. and 0.38 g of porcine trypsin in 6.84 ml of 0.05M calcium acetate was added. After 48 hours at 12° C. the proteins were precipitated with acetone as described in Example 6.

The derivative was purified by HPLC using first 1800 ml eluent composed of 35 parts of ethanol and 65 parts of aqueous 0.3M KCl, 0.001N HCl, followed by an eluent composed of 37 parts of ethanol and 63 parts of the aqueous solution. The derivative emerged 10 minutes after shift in eluent and it was isolated as described for $Gln^{A17}, Lys^{B30}-NH_2$ human insulin Example 6. Finally it was purified on a column of SP-Sephadex ™ C-25 as described for $Gln^{A17}, Lys^{B30}-NH_2$ human insulin in Example 7.

The yield of $Arg^{B27}, Thr^{B30}-NH_2$ human insulin was 1.63 g corresponding to 43%. Essentially one band was seen in DISC PAGE electrophoresis, the rate of migrating being 55% of that of insulin. In analytical HPLC the product emerge before porcine insulin, the purity being about 96%. Amino acid composition analysis shows 2 arginine and 2 threonine residues per molecule, and otherwise identity to human insulin.

EXAMPLE 9

Synthesis of $Arg^{B27}, Lys^{B30}-NH_2$ human insulin

The compound was synthesized from 3.61 g of $Arg^{B27}, B(1-29)$—Ala—Ala—Lys—A(1—21) insulin precursor using the methods described in Example 7. Yield of $Arg^{B27}, Lys^{B30}-NH_2$ human insulin 0.78 g =22%. One major band in DISC PAGE electrophoresis migrating 35% of the distance of insulin migration. Two minor bands visible. Purity in analytical HPLC 92%; the product emerge before porcine insulin Amino acids composition analysis shows 2 arginine, 2 lysine and 1 threonine residues per molecule and otherwise identity to human insulin.

EXAMPLE 10

Synthesis of $Lys^{B27}, Thr^{B30}-NH_2$ human insulin

The compound was synthesized from 7.0 g of $Lys^{B27}, B(1-29)$—Ala—Ala—Lys—A(1—21) insulin precursor using the methods described in Example 8. Yield of $Lys^{B27}, Thr^{B30}-NH_2$ human insulin was 3.15 g corresponding to 45%. DISC PAGE electrophoresis showed one major band and two minor bands, the main band migrating 55% of the distance of the insulin reference band. The purity in analytical HPLC was 96%. The compound emerge earlier than porcine insulin in reverse phase HPLC. Amino acid composition analysis shows 2 lysine and 2 threonine residues per molecule and otherwise identity to human insulin.

EXAMPLE 11

Synthesis of $Lys^{B27}, Lys^{B30}-NH_2$ human insulin

The compound was synthesized from 7.0 g of $Lys^{B27}, B(1-29)$—Ala—Ala—Lys—A(1—21) insulin precursor using the methods described in Example 7. Yield of $Lys^{B27}, Lys^{B30}-NH_2$ human insulin was 1.57 g corresponding to 22%. DISC PAGE electrophoresis showed one major band migrating to a distance of 35% of that of porcine insulin One minor impurity is visible. Purity in analytical HPLC was 94%, the compound eluting well ahead of porcine insulin. Amino acid composition analysis showed 3 lysine and 1 threonine residues per molecule and otherwise identity to human insulin.

EXAMPLE 12

Synthesis of $Gln^{B13},Thr^{B30}$—$NH_2$ human insulin

The compound was synthesized from 3.05 g of $Gln^{B13}$,B(1—29)—Ala—Ala—Lys—A(1—21) insulin precursor using the methods described in Example 8. Yield of final product was 0.88 g corresponding to 29%. DISC PAGE electrophoresis showed one major band, migrating 55% of the distance porcine insulin migrates. Purity by HPLC was 95%, the compound eluting later than porcine insulin. Amino acid composition analysis showed identity to that of human insulin.

EXAMPLE 13

Preparation of injectable solutions of compounds of formula I

Sterile injectable solutions of the compounds of formula I for testing of the degree of prolonged action were made using 1.6% (w/v) glycerol as the isotonicum, using 0.3% (w/v) m-cresol as the preservative, and being buffered with 0.01 M sodium acetate The concentration of zinc ions was 8 or 80 µg/ml. The pH values of the solutions were adjusted sufficiently off the isoelectric point of the compounds of formula I to keep the solutions clear upon storage at 4° C. The solutions contained 240 nmole/ml of the compounds of formula I. The concentration of 240 nmole/ml was established by measurement of the absorbance at 276 nm of a more concentrated stock solution devoid of m-cresol, using the molar extinction coefficient for porcine insulin of 6100 for these derivatives (see Handbuch der Inneren Medizin, Vol. 7/Part 2A, Editor: Oberdisse, 1975, 113). For monocomponent porcine insulin, the established potency is 28.5 U/mg dry substance (see Diabetes Care, Vol. 6/Supplement 1 (1983), 4), viz. 1 U corresponds to 5.95 nmole.

Injectable solutions containing 240 nmole/ml of the compounds of formula I stated in Table II and having the pH values and content of zinc stated therein were made.

Test for prolongation of insulin effect

The prolongation of the hypoglycemic effect produced by the injectable solutions of insulin was tested according to British Pharmacopoeia 1980, A 142, in fasted rabbits. Each test solution was administered subcutaneously in a dosis of 14.3 nmole per rabbit in 12 animals weighing 3–4 kg, and the course of the hypoglycemia was followed for 6 hours. For comparison the fast acting porcine insulin, and the ACTRAPID ™ porcine insulin, and the intermediate acting, MONOTARD ™ human insulin, were included in the tests. The results of the tests are shown in Table II.

TABLE II

| Compound of formula I | $Zn^{++}$, µg/ml | pH | \multicolumn{4}{c}{Glucose in percent of initial} |
|---|---|---|---|---|---|---|
| | | | 1 h | 2 h | 4 h | 6 h |
| $Gln^{417},Arg^{B27}$ insulin | 80 | 4.5 | 53 | 47 | 50 | 66 |
| $Gln^{B13},Arg^{B27}$ insulin | 80 | 4.5 | 55 | 46 | 61 | 91 |
| $Gln^{417},Gln^{B13}$ insulin | 80 | 4.5 | 53 | 47 | 55 | 82 |
| $Arg^{B27}$ insulin | 80 | 4.5 | 45 | 34 | 51 | 91 |
| $Lys^{B27}$ insulin | 80 | 4.5 | 47 | 40 | 55 | 93 |
| $Gln^{417},Thr^{B30}$—$NH_2$ insulin | 80 | 4.5 | 65 | 63 | 68 | 83 |
| $Gln^{417},Lys^{B30}$—$NH_2$ insulin | 80 | 4.5 | 60 | 56 | 73 | 86 |
| $Gln^{B13},Thr^{B30}$—$NH_2$ insulin | 6.7 | 4.5 | 91 | 92 | 92 | 90 |
| $Arg^{B27},Thr^{B30}$—$NH_2$ insulin | 80 | 4.5 | 88 | 86 | 85 | 81 |
| $Arg^{B27},Thr^{B30}$—$NH_2$ insulin | 8.5 | 4.5 | 62 | 64 | 66 | 67 |
| $Arg^{B27},Lys^{B30}$—$NH_2$ insulin | 80 | 4.5 | 85 | 83 | 81 | 79 |

TABLE II-continued

| Compound of formula I | $Zn^{++}$, µg/ml | pH | \multicolumn{4}{c}{Glucose in percent of initial} |
|---|---|---|---|---|---|---|
| | | | 1 h | 2 h | 4 h | 6 h |
| $Arg^{B27},Lys^{B30}$—$NH_2$ insulin | 10.9 | 4.5 | 78 | 73 | 69 | 67 |
| $Lys^{B27},Thr^{B30}$—$NH_2$ insulin | 7.4 | 4.5 | 56 | 55 | 62 | 61 |
| $Lys^{B27},Lys^{B30}$—$NH_2$ insulin | 9.5 | 4.5 | 72 | 65 | 65 | 60 |
| $Lys^{B30}$—$NH_2$ insulin | 80 | 4.5 | 74 | 83 | 80 | 82 |
| Actrapid ™ porcine insulin | 15 | 7 | 58 | 56 | 87 | 100 |

Except for ACTRAPID, the insulin species is human.

The potencies of insulin compounds were accessed in the mouse blood sugar depletion test (British Pharmacopoeia 1980, A 141-A 142). In order to minimize the problem of estimating potency of insulins having a timing different from the standard, insulin solutions for potency determinations were made up without additions of zinc. Solutions were made up to contain 240 nmole/nl based on the absorbance at 276 nm. The zinc content of solutions were 8–10 µg/ml, arising from the crystalline derivatives. The estimated potencies of some insulin compounds are shown in Table III, below.

TABLE III

| | Potency relative to insulin, % | Confidence limits (P = 0.05), % |
|---|---|---|
| $Gln^{417},Thr^{B30}$—$NH_2$ insulin | 67 | 58–75 |
| $Gln^{417},Lys^{B30}$—$NH_2$ insulin | 62 | 51–72 |
| $Arg^{B27},Thr^{B30}$—$NH_2$ insulin | 92 | 99–85 |
| $Arg^{B27},Lys^{B30}$—$NH_2$ insulin | 84 | 74–94 |
| $Gln^{417},Arg^{B27}$ insulin | 69 | 79–62 |
| $Gln^{B13},Arg^{B27}$ insulin | 78 | 88–69 |
| $Gln^{B13},Gln^{417}$ insulin | 50 | 63–40 |
| $Arg^{B27}$ insulin | 87 | 95–80 |
| $Lys^{B27}$ insulin | 88 | 97–80 |
| $Gln^{B21}$ insulin | 96 | |
| $Gln^{44}$ insulin | 79 | |
| $Lys^{B27},Thr^{B30}$—$NH_2$ insulin | 82 | 89–76 |
| $Lys^{B27},Lys^{B30}$—$NH_2$ insulin | 56 | 69–50 |
| $Gln^{417},Arg^{B27},Thr^{B30}$—$NH_2$ insulin | 71 | 79–63 |
| $Gln^{B13},Arg^{B27},Thr^{B30}$—$NH_2$ insulin | 62 | 71–55 |
| $Gln^{417},Gln^{B13},Thr^{B30}$—$NH_2$ insulin | 49 | 60–40 |

The description in European Application Publication No. 163,529 is as follows:

1. Preparation of a gene coding for human proinsulin B-C-A

Total RNA. purified (Chirgwin, J. M. Przybyla, A. E., McDonald, R. J. & Rutter, W. J., Biochemistry 18, (1979) 5294–5299) from human pancreas was reverse transcribed (Boel, E., Vuust, J., Norris, F., Norris, K., Wind, A., Rehfeld, J. F. & Marcker, K. A., Proc. Natl. Acad. Sci. U.S.A. 80, (1983), 2866–2869) with AMV reverse transcription and d(GCTTTATT-CCATCTCTC) as 1. strand primer. After preparative urea-polyacrylamide gel purification of the human proinsulin cDNA, the second strand was synthesized on this template with DNA polymerase large fragment and d(CAGATCACTGTCC) as 2nd strand primer. After S1 nuclease digestion the human proinsulin ds. cDNA was purified by polyacrylamide gel electrophoresis, tailed with terminal transferase and cloned in the PstI site on pBR327 (Sorberon et al., Gene 9, (1980) 287–305) in E. coli. A correct clone harbouring a plasmid containing a gene encoding human proinsulin B-C-A was identified from the recombinants by restriction endonuclease analysis and confirmed by nucleotide sequencing (Maxam, A., & Gilbert, W., Methods in Enzymology, 65 (1980), 499–560. Sanger, F., Nicklen, S. & Coulson, A. R., Proc. Natl. Acad. Sci. U.S.A., 74, (1977), 5463–5467). 2. Preparation of genes coding for precursors of human insulin.

The gene encoding B(1-29)-A(1-21) of human insulin was made by site specific mutagenesis of the human proinsulin sequence with a 75bp in frame deletion in the C-peptide coding region inserted into a circular single stranded M-13 bacteriophage vecter. A modified procedure (K. Norria et al., Nucl. Acids. Res. 11 (1983) 5103–5112) was used in which a chemically synthesized 19-mer deletion primer was annealed to the M13 template. After a short enzymatic extension reaction a "universal" 15-mer M13 dideoxy sequentially primer was added followed by enzymatic extension and ligation. A double stranded restriction fragment (BamHl-Hind III) was cut out of the partly double stranded circular DNA and ligated into pBR322 cut with BamHI and Hind III.

The obtained ligation mixture was used to transform *E. coli* and transformants harbouring a plasmid pMT319 containing the gene encoding B(1-29)-A-(1-21) of human insulin were identified.

Genes encoding B(1-29)—Ala—Ala—Lys—A(1-21) and B(1-29)—Ser—Lys—A(1—21) and B(-29)-Ser-Lys-A(1-21) were made accordingly by insertion of a fragment encoding MFα1-B-C-A in the M-13 bacteriophage and site specific mutagenesis of the human proinsulin sequence with chemically synthesized 30-mer and 27-mer deletion primers, respectively, and the above mentioned "universal" 15-mer M13 dideoxy sequencing primer. A double stranded restriction fragment (XbaI-EcoRl) was cut out of the partly double stranded circular DNA and ligated into pUCI3 and pT5, respectively. By transformation and retransformation of *E. coli*, transformants harbouring a plasmid pMT598 containing the gene encoding B(1-29)-Ala-Ala-Lys-A(1-21) and pMT630 containing the gene encoding B(1-29)-Ser-Lys-A(1-21) were identified.

A gene encoding B(1-29)-Thr-Arg-Glu-Ala-Glu-Asp-Leu-Gln-Lys-A(1-21) was made in a similar way as described above by insertion of a fragment encoding MFα1-B(1-29)-A(1-21) in a M13 mp11 bacteriophage and site specific mutagenesis of the B(1-29)-A(1-21) sequence with a chemically synthesized 46-mer deletion primer (5'CACACCCAAGACTAAAGAAGCT-GAAGACTTGCAAAGAGGCATTGTG-3') and the "universal" primer. Also, by a similar procedure a gene encoding B(1-29)—Thr—Arg—Glu—Ala—Glu—Asp—Leu—Gln—Val—Gly—Gln—Val—Glu—Leu—Gly—Gly—Gly—Pro—Gly—Ala—Gly—Ser—Leu—Gln—Pro—Leu—Ala—Leu—Glu—Gly—Ser—Leu—Gln—Lys—A(1-21) was constructed 3. Plasmid constructions.

The gene encoding B(1-29)-A-(1-21) of human insulin (B'A) was isolated as a restriction fragment from pMT319 and combined with fragments coding for the TPI promoter (TPI$_P$) (T. Alber and G Kawasaki, Nucleotide Sequence of the Triose Phosphate Isomerase Gene of *Saccharomyces cerevisiae*. J.Mol. Applied Genet. 1 (1982) 419–434), the MFα1 leader sequence (J. Kurjan and I. Herskowitz,. Structure of a Yeast Pheromone Gene (MFα): A Putative α-Factor Precursor Contains four Tandem Copies of Mature α-Factor. Cell 30 (1982) 933–943) and the transcription termination sequence from TPI of *S. cerevisiae* (TPI$_T$). These fragments provide sequences to ensure a high rate of transcription for the B'A encoding gene and also provide a presequence which can effect the localization of B'A into the secretory pathway and its eventual excretion into the growth medium. This expression unit for B'A (TPI$_P$-MFα1 leader - B'A-TPI$_T$ was then placed on a plasmid vector containing the yeast 2μ origin of replication and a selectable marker, LEU 2, to give pMT344, a yeast expression vector for B'A.

During in vivo maturation of α-factor in yeast, the last (C-terminal) six amino acids of the MFα1 leader peptide (Lys—Arg—Glu—Ala—Glu—Ala) are removed from the α-factor precursor by the sequential action of an endopeptidase recognizing the Lys-Arg sequence and an aminodipeptidase which removes the Glu-Ala residuals (Julius, D. et al. Cell 32 (1983) 839–852). To eliminate the need for the yeast aminodipeptidase, the sequence coding for the C-terminal Glu—Ala—Glu—Ala of the MFα1 leader was removed via in vitro mutagenesis. The resulting yeast expression plasmid, pMT475, contains the insert coding for TPI$_P$-MFα1 leader (minus Glu—Ala—Glu—Ala)—B'A—TPI$_T$.

In a preferred construction the modified expression unit was transferred to a stable, high copy number yeast plasmid CPOT, (ATCC No. 39685), which can be selected merely by the presence of glucose in the growth medium. The resulting yeast expression vector for B'A was numbered pMT479.

The fragment encoding MFα1 leader (minus Glu—Ala—Glu—Ala)-B(1-29)—Ala—Ala—Lys—A(1-21) was isolated as a restriction fragment from pMT598 and combined with fragments coding for the TPI promoter and the TPI terminator and transferred to the above mentioned high copy number yeast plasmid CPOT. The resulting yeast expression vector for B(1-29)—Ala—Ala—Lys—A(1-21) was numbered pMT610.

The fragment containing the insert TPI$_P$-MFα1 leader (minus Glu—Ala—Glu—Ala)-B(1—29-)—Ser—Lys—A(1—21)—TPI$_T$ was isolated as a restriction fragment from pMT630 and transferred into CPOT. The resulting yeast expression vector for B(1—29)—Ser—Lys—A(1—21) was numbered pMT639.

The fragment containing the insert TPI$_P$—MFα1 leader (minus Glu—Ala—Glu—Ala)—B(1—29)—Thr—Arg—Glu—Ala—Glu—Asp—Leu—Gln—Lys—A(1—21)TPI$_T$ was inserted into a high copy number yeast plasmid DPOT, being a CPOT derivative containing a SphI-BamHI fragment of PBR322 inserted into a SpHI-BamHI fragment of CPOT. The resulting yeast expression vector for B(1—29)—Thr—Arg—Glu—Ala—Glu—Asp—Leu—Gln—Lys—A(1—21) was numbered p1126.

4. Transformation

Plasmids pMT344 and pMT475 were transformed into *S. cerevisiae* leu 2 mutants by selection for leucin prototrophy as described by Hinnen et al. (A. Hinnen, J. B. Hicks and G. R. Fink. Transformation of Yeast. Proc.Nat.Aca.Sci 75 (1978) 1929).

Plasmids pMT479, pMT610, pMT639 and p1126 were transformed into *S. cerevisiae* strains carrying deletions in the TPI gene by selecting for growth on glucose. Such strains are normally unable to grow on glucose as the sole carbon source and grow very slowly on galactose lactate medium. This defect is due to a mutation in the triose phosphate isomerase gene, obtained by deletion and replacement of a major part of this gene with the *S. cerevisiae* LEU 2 gene. Because of the growth deficiencies there is a strong selection for a plasmid which contains a gene coding for TPI pMT479 contains the *Schizo. pombe* TPI gene.

5. Expression of human insulin precursor in yeast

Expression products of human insulin type were measured by radioimmunoassay for insulin as described by Heding, L. (Diabetologia 8, 260-66, 1972) with the only exception that the insulin precursor standard in question was used instead of an insulin standard. The purity of the standards were about 98% as determined by HPLC and the actual concentration of peptide in the standard was determined by amino acid analysis. The expression levels of immunoreactive human insulin precursors in the transformed yeast strains are summarized in Table 1.

TABLE 1

Expression levels of immunoreactive human insulin precursors in yeast.

| Yeast strain | Plasmid | Construct | Immunoreactive insulin precursor (nmol/l supernatant) |
|---|---|---|---|
| MT 350 (DSM 2957) | pMT 344 | B(1-29)—A(1-21) | 100 |
| MT 371 (DSM 2958) | pMT 475 | B(1-29)—A(1-21) | 192 |
| MT 519 (DSM 2959) | pMT 479 | B(1-29)—A(1-21) | 2900 |
| MT 620 (DSM 3196) | pMT 610 | B(1-29)—Ala—Ala—Lys—A(1-21) | 1200-1600 |
| MT 649 (DSM 3197) | pMT 639 | B(1-29)—Ser—Lys—A(1-21) | 1600 |
| ZA 426 | p1126 | B(1-29)—Thr—Arg—Glu—Ala—Glu—Asp—Leu—Gln—Lys—A(1-21) | 200 |

6. Conversion of human insulin precursor into B30 esters of human insulin

The conversion of the human insulin precursors into human insulin esters can be followed quantitatively by HPLC (high pressure liquid chromatography) on reverse phase A 4×300 mm "μBondapak C18 column" (Waters Ass.) was used and the elution was performed with a buffer comprising 0.2M ammonium sulphate (adjusted to a pH value of 3.5 with sulphuric acid) and containing 26-50% acetonitrile. The optimal acetonitrile concentration depends on which ester one desires to separate from the insulin precursor. In case of human insulin methyl ester separation is achieved in about 26% (v/v) of acetonitrile.

Before the application on the HPLC column the proteins in the reaction mixture were precipitated by addition of 10 volumes of acetone. The precipitate was isolated by centrifugation, dried in vacuo, and dissolved in 1M acetic acid.

The address of DSM is: Deutsche Sammlung von Mikro-Organismen (DSM), Grisebachstr. 8, D-3400 Gottingen, West Germany.

What is claimed:

1. A human insulin analog having one or more of the following amino acid residue substitutions:

A neutral amino acid residue selected from the group consisting of: Gly, Val, Ile, Leu, Phe, Tyr, Met, Asn, Gln, Ala, Ser and Thr instead of Glu at any of the positions A4, A17, B13 and B21 and Lys or Arg instead of $Thr^{B27}$ and said insulin analog having at least one positive charge more than human insulin at a pH value of 7.

2. Compound according to claim 1, characterized in that A4, A17 and B21 each is a glutamic acid residue.

3. Compounds according to claim 1, characterized in that B13 is a glutamine residue.

4. An insulin analog selected from the group consisting of
$Gln^{A17},Arg^{B27},Thr^{B30}$—$NH_2$ human insulin, $Gln^{A17},Gln^{B13},Thr^{B30}$—$NH_2$ human insulin, $Gln^{A17},Lys^{B27},Thr^{B30}$—$NH_2$ human insulin, $Gln^{A17},Lys^{B30}$—$NH_2$ human insulin, $Gln^{A17},Thr^{B30}$—$NH_2$ human insulin, $Gln^{B13},Arg^{B27},Thr^{B30}$—$NH_2$ human insulin, $Gln^{B13},Lys^{B27},Thr^{B30}$—$NH_2$ human insulin, $Gln^{B30},Lys^{B30}$—$NH_2$ human insulin, $Gln^{B13},Thr^{B30}$—$NH_2$ human insulin, $Arg^{B27},Arg^{B30}$—$NH_2$ human insulin, $Arg^{B27},Lys^{B30}$—$NH_2$ human insulin, $Arg^{B27},Thr^{B30}$—$NH_2$ human insulin, $Lys^{B27},Arg^{B30}$—$NH_2$ human insulin, $Lys^{B27},Lys^{B30}$—$NH_2$ human insulin or $Lys^{B27},Thr^{B30}$—$NH_2$ human insulin.

5. An insulin analog according to claim 1 wherein the neutral amino acid residue is selected from the group consisting of: Asn, Gln, Ala, Ser and Thr.

6. An injectable aqueous insulin solution characterized by prolonged insulin action containing an effective amount of a human insulin analog having one or more of the following amino acid residue substitutions:

A neutral amino acid residue selected from the group consisting of: Gly, Val, Ile, Leu, Phe, Tyr, Met, Asn, Gln, Ala, Ser and Thr instead of Glu at any of the positions A4, A17, B13 and B21 and Lys and Arg instead of $Thr^{B27}$, said insulin analog having at least one positive charge more than human insulin at a pH value of 7; and said injectable solution having a pH value in the range of pH 4.5-8.

7. A human insulin analog having one or more of the following amino acid residue substitutions:

A neutral amino acid residue selected from the group consisting of: Gly, Val, Ile, Leu, Phe, Tyr, Met, Asn, Gln, Ala, Ser and Thr instead of Glu at any of the positions A4, A17, B13 and B21, and Lys or Arg instead of $Thr^{B27}$, and said insulin analog further having Lys—$NH_2$ or Thr—$NH_2$ at B30.

* * * * *